United States Patent
El-Gabry et al.

(10) Patent No.: US 6,585,408 B2
(45) Date of Patent: Jul. 1, 2003

(54) METHOD AND APPARATUS FOR MEASURING LOCAL HEAT TRANSFER DISTRIBUTION ON A SURFACE

(75) Inventors: Lamyaa Abdel Alle El-Gabry, Schenectady, NY (US); Steven J. Brzozowski, Scotia, NY (US); Nirm V. Nirmalan, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/916,345

(22) Filed: Jul. 30, 2001

(65) Prior Publication Data

US 2003/0021329 A1 Jan. 30, 2003

(51) Int. Cl.$^7$ .............................................. G01N 25/20
(52) U.S. Cl. ............................ 374/43; 374/44; 374/162
(58) Field of Search ............................. 374/43, 44, 162

(56) References Cited

U.S. PATENT DOCUMENTS

| | | | | |
|---|---|---|---|---|
| 4,309,901 A | * | 1/1982 | Rolinski et al. ................. 374/1 |
| 4,902,139 A | * | 2/1990 | Adiutori ...................... 374/137 |
| 4,906,581 A | * | 3/1990 | Baker et al. ................. 436/147 |
| 4,916,715 A | * | 4/1990 | Adiutori ........................ 374/1 |
| 4,978,230 A | * | 12/1990 | Adiutori et al. ............. 374/145 |
| 5,067,977 A | * | 11/1991 | Deb .......................... 65/29.18 |
| 5,161,889 A | * | 11/1992 | Smith et al. ................. 219/399 |
| 5,526,148 A | * | 6/1996 | Moffat et al. ................. 349/20 |
| 5,533,864 A | * | 7/1996 | Nomoto et al. ............... 416/96 A |
| 5,580,172 A | * | 12/1996 | Bhardwaj et al. ............ 374/137 |
| 5,649,766 A | * | 7/1997 | Blake .......................... 374/137 |
| 6,422,743 B1 | * | 7/2002 | Nirmalan et al. ............ 250/330 |
| 2002/0006152 A1 | * | 1/2002 | Prasad et al. .................. 374/44 |

OTHER PUBLICATIONS

Florschuetz et al., "Streamwise Flow and Heat Transfer Distributions for Jet Array Impingement with Crossflow", Journal of Heat Transfer, Transactions of the ASME, vol. 103, May 1981, pp. 337–342.

Huang et al., "Detailed Heat Transfer Distributions Under an Array of Orthogonal Impinging Jets", Journal of Thermophysics and Heat Transfer, vol. 12, No. 1, Jan.–Mar. 1998, pp. 73–78.

K. P. Perry, "Heat Transfer by Convection from a Hot Gas Jet to a Plane Surface", IME Proc. 1954, pp. 775–784.

* cited by examiner

Primary Examiner—Diego Gutierrez
Assistant Examiner—Lydia M. De Jesús
(74) Attorney, Agent, or Firm—Nixon & Vanderhye

(57) ABSTRACT

An apparatus and method for measuring local heat transfer distribution of an object surface. The apparatus includes a heater element for providing heat flux, a member disposed on a surface of the heater element for receiving impinging cooling air. A liquid crystal element is provided on a side of the heater element remote from the surface, and an insulating material is disposed adjacent to the liquid crystal element and remote from the heater element. The apparatus further includes means for determining heat transfer distribution coefficients from the liquid crystal element.

23 Claims, 8 Drawing Sheets

Arrays of Jets

Slotted Jets

METHOD AND APPARATUS FOR MEASURING LOCAL HEAT TRANSFER DISTRIBUTION ON A SURFACE

BACKGROUND OF THE INVENTION

The present invention relates to apparatus and methods for measuring heat transfer distributions on a surface and obtaining surface heat transfer data for a variety of cooling jet impingement configurations on the surface at different Reynolds numbers and particularly relates to apparatus and methods for determining local heat transfer distribution and Nusselt numbers for the heat transfer coefficients.

In many industrial applications, it is important to have detailed information concerning the heat transfer characteristics of a surface, especially in product design, as they enable a design engineer to better predict and understand thermal gradients, non-uniformity and other characteristics of heat transfer distribution which current methods cannot provide. For example, in industrial applications such as a gas turbine, a surface cooled by impingement of air jets can result in non-uniform surface temperatures and high temperature gradients. The temperature gradients, however, cannot be ascertained without knowing the temperature distribution of the surface of interest. Average surface temperatures fail to describe the temperature gradients or the non-uniformity of heat transfer that may exist. Both can be detrimental to a design. For example, a design which meets average temperature requirements may fail due to thermal fatigue if the temperature gradients are high.

In one approach, thermocouples have been mounted to a surface being cooled and used to measure temperature. However, there temperature measurements are a function of the locations of the thermocouples. If the thermocouple is positioned beneath an impinging jet of cooling air, it will read a higher temperature than if located between jets of impinging cooling air. Thus, the thermocouple may not accurately reflect the temperature of the surface. The thermocouple reading is often reported as a mean temperature, which is not correct because the thermocouple only averages temperature locally rather than along the entire surface.

In one prior report, a transient liquid crystal technique was used to measure heat transfer under an array of orthogonal jets. A thin coating of liquid crystal was sprayed on the impingement surface. The jet Reynolds numbers tested were between 4,800 and 18,300, the latter Reynolds number being a fairly low number. Moreover, the technique employed was transient rather than steady state. Additionally, the liquid crystal spray can be unreliable if not applied correctly. In any event, such research was limited to orthogonal impinging jets. See Huang, Y., Ekkad, S., and Han, J., "Detailed Heat Transfer Distribution Under an Array of Orthogonal Impinging Jets," *Journal of Thermophysics and Heat Transfer*, Vol. 12, No. 1, January-March 1998.

Another technique measured the effect of a jet angle from a single jet of hot air impinging on a water cooled impingement plate. A calorimeter measured the rise in temperature of a metered flow of water from which the heat flow was determined and ultimately the heat transfer distribution on the plate was derived. This data, however, is derived using only a single jet of hot air whereas arrays of jets are more common in practice. Accordingly, there is a need for an apparatus and methods for quantitatively describing local heat transfer effects.

BRIEF SUMMARY OF THE INVENTION

In accordance with a preferred embodiment of the present invention, there is provided an apparatus and method for determining local heat transfer distribution for a surface being cooled using an array of impinging jets, both orthogonal and angled relative to the surface, employing a broadband liquid crystal as a temperature sensor, air as a cooling medium, and a thin foil heater to provide constant heat flux for measuring both smooth and roughened surfaces over a range of jet Reynolds numbers between 10,000 and 35,000. The apparatus is also capable of achieving higher ranges of jet Reynolds numbers.

The apparatus employs a pressure chamber for flowing air under pressure through orifices of a jet plate at constant angles to provide either orthogonal or angled impingement air jets onto a smooth or rough surface. The surface is preferably heated using a thin foil heater adhered directly to the bottom of the test plate surface to provide a constant heat flux boundary condition. A calibrated liquid crystal sheet is mounted on the side of the heater element remote from the surface. Preferably, an insulating cover is placed on the liquid crystal face to reduce heat losses while enabling visual observation of the temperature, i.e., color fields, of the impingement surface. The plenum, jet plate, test plate, heater, liquid crystal and insulating material are placed in a pressure vessel, and enabling control of the pressure ratio across the plate, enabling the tests to be run at higher jet Reynolds numbers than possible if air was discharged directly into atmosphere. A camera is used to capture the images through a window of the pressure vessel and insulating material.

With the supply of air in the pressure vessel controlled to a particular temperature and pressure, liquid crystal temperature profiles are digitally recorded by computer and an image analysis system converts the liquid crystal image data into temperature distributions. A calibration curve is first generated by applying a temperature gradient between opposite ends of a liquid crystal strip and obtaining temperature measurements at equal distances along the strip. The calibration curve is digitized. Using the digitized calibration curve, a text file containing temperature at each pixel in the image captured is created. The text file contains a two-dimensional array of data, the intersection of each row and column representing a single pixel. This text file is then transformed into heat transfer coefficients and Nusselt numbers. Because the liquid crystal operates over a broad band of temperature, e.g., 5° or less, and since surface temperature variations are greater than the bandwidth of the liquid crystal, several images are taken at various heat flux levels to provide a color change in each element of the liquid crystal. The images are superimposed and averaged to yield the heat transfer distribution on the entire surface—assuming that the heat transfer coefficients are not a function of heat flux.

To determine the heat transfer coefficient distribution, the partial distributions of the individual images are averaged. Thus, the heat transfer coefficient distribution for a first image and all subsequent images are recorded. The average heat transfer coefficient at each pixel for all images taken is likewise recorded. Once the overall heat transfer coefficient is obtained, the overall Nusselt number distribution for the surface based on this overall average heat transfer coefficient is determined. These steps may be repeated for each plate configuration at each Reynolds number, i.e., for plate configurations having jet impingement angles of 90°, 60°, 30° or the like.

In one aspect, the present invention provides a method of measuring local heat transfer characteristics of an object surface, the method comprising the steps of flowing a cooling medium onto the surface; sensing the temperature of the surface by juxtaposing a liquid crystal element and the surface; measuring temperature distributions of each pixel of the liquid crystal element at various heat flux levels; processing the temperature distributions to obtain temperature distribution profiles at each heat flux level; determining heat transfer coefficients of each pixel at each heat flux level; and determining an average heat transfer coefficient profile at each pixel. The method further includes determining an overall Nusselt number from the average heat transfer coefficient profile, calibrating the liquid crystal element prior to the processing step to determine temperature distribution profiles. The method further includes saving the temperature distribution profiles and filtering the heat transfer coefficients at each pixel to remove artificially negative data points.

In another aspect, in an apparatus comprising a heater element and a liquid crystal element juxtaposed in temperature sensing relation to an object surface, a method of measuring local heat transfer distribution along the surface comprising the steps of: obtaining steady state images of the liquid crystal element as a function of the sensed temperature of the surface at various heat flux levels; processing the steady state images to determine temperature distribution profiles at each pixel along the liquid crystal element; determining heat transfer coefficients for each temperature distribution profile; and determining an average heat transfer coefficient profile.

In a further aspect, a method for measuring local heat transfer distribution of an object surface, the method comprising the steps of: directing cooling air onto the surface; providing a liquid crystal element on a side of a heater element remote from the surface; energizing said heater element to various heat flux levels; measuring temperature distributions of various pixels of the liquid crystal element at the various heat flux levels; processing said temperature distributions to obtain temperature distribution profiles; and obtaining heat transfer coefficients for each distribution profile.

In yet another aspect, an apparatus for measuring local heat transfer distribution of an object surface, comprising a heater element for providing heat flux; a test plate disposed on a surface of the heater element for receiving impinging cooling air; a liquid crystal element on a side of the heater element remote from the surface; an insulating material disposed adjacent to the liquid crystal element and remote from the heater element; and means for determining heat transfer distribution coefficients from said liquid crystal element. The heater element preferably is a thin foil heater. The insulating element may be formed of a transparent material. The apparatus further includes a liquid crystal video thermographic system for capturing images of the liquid crystal element at various heat flux levels, and a computer system for controlling and monitoring various elements of the apparatus. The computer system preferably includes a memory device to store images of the liquid crystal element.

In yet another aspect, an apparatus for measuring local heat transfer distribution of an object surface, comprising: a liquid crystal element; a heater element for heating the liquid crystal element to various heat flux levels; the liquid crystal element disposed adjacent to the heater element for measuring heat transfer distributions of the object surface; means for capturing images of the liquid crystal element at each heat flux level; and means for determining heat transfer coefficients from the captured images.

In another aspect, an apparatus for measuring local heat transfer characteristics of an object surface, comprising: means for flowing a cooling medium onto the surface; means for sensing the temperature of the surface by juxtaposing a liquid crystal element and the surface; means for measuring temperature distributions of each pixel of the liquid crystal element at various heat flux levels; means for processing the temperature distributions to obtain temperature distribution profiles at each heat flux level; means for determining heat transfer coefficients of each pixel at each heat flux level; and means for determining an average heat transfer coefficient profile at each pixel. The apparatus further includes means for determining Nusselt numbers from the average heat transfer coefficient profiles.

DETAILED DESCRIPTION OF THE INVENTION

Figure 1:
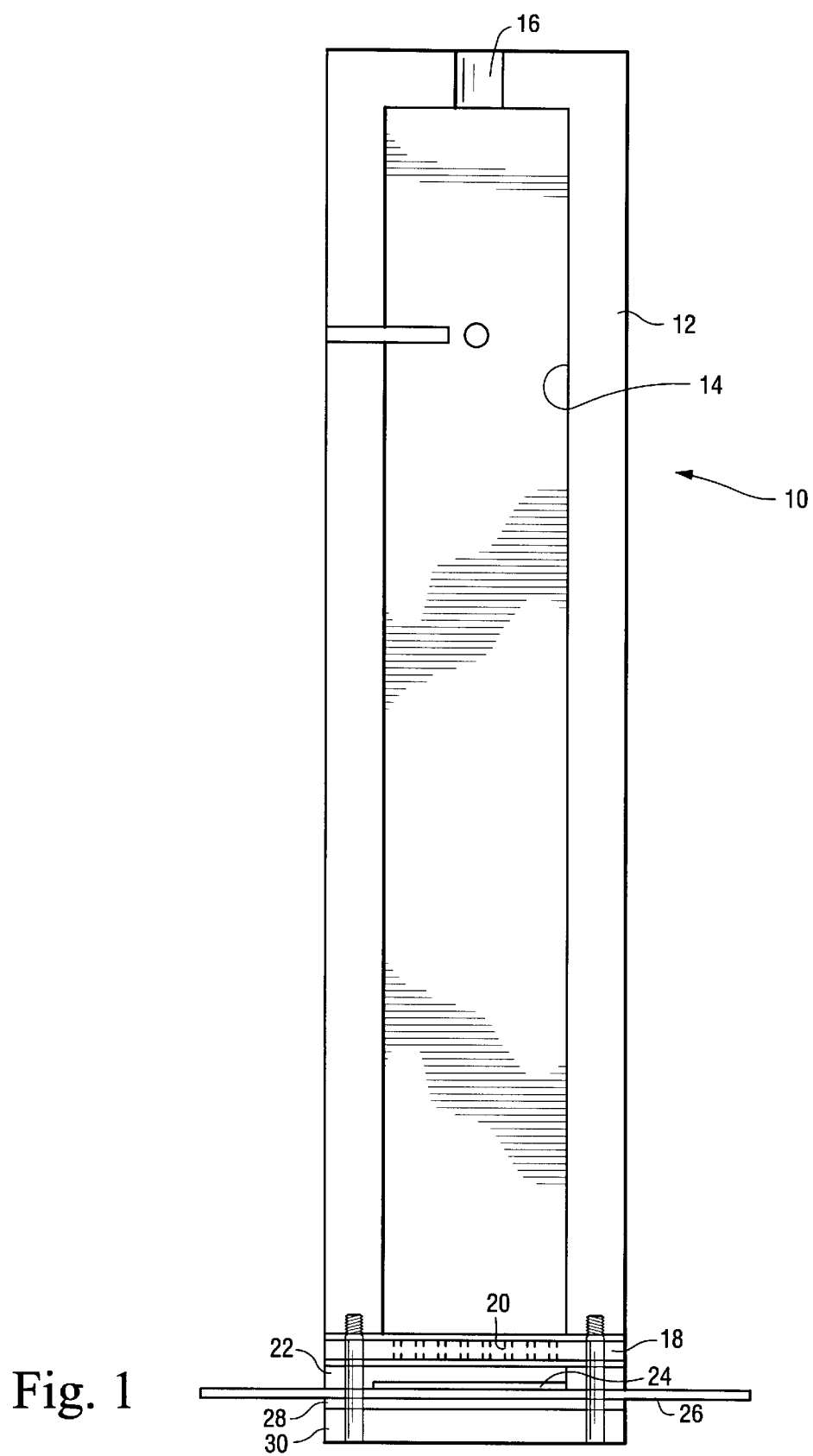
FIG. 1 is a cross-sectional view of a test plenum for measuring local heat transfer distribution on a surface under an array of impingement jets in accordance with a preferred embodiment of the present invention.

Referring to the drawings, particularly to FIG. 1, there is illustrated a test plenum for measuring local heat transfer distribution on a surface under an array of impinging jets. The test plenum, generally designated 10, includes a generally elongated housing 12 defining a generally elongated rectilinear chamber 14 having an inlet 16 at one end for receiving air under pressure. At the opposite end of the housing 12 and in communication with the chamber 14 is a jet plate 18 having a plurality of orifices 20 through which the air under pressure within chamber 14 passes onto a test plate. The orifices 20, while illustrated in FIGS. 1 and 4 as disposed normal to the planar surface of the jet plate, may be angled relative thereto, for example, at 30° or 60° or other angles as desired.

Figure 2:
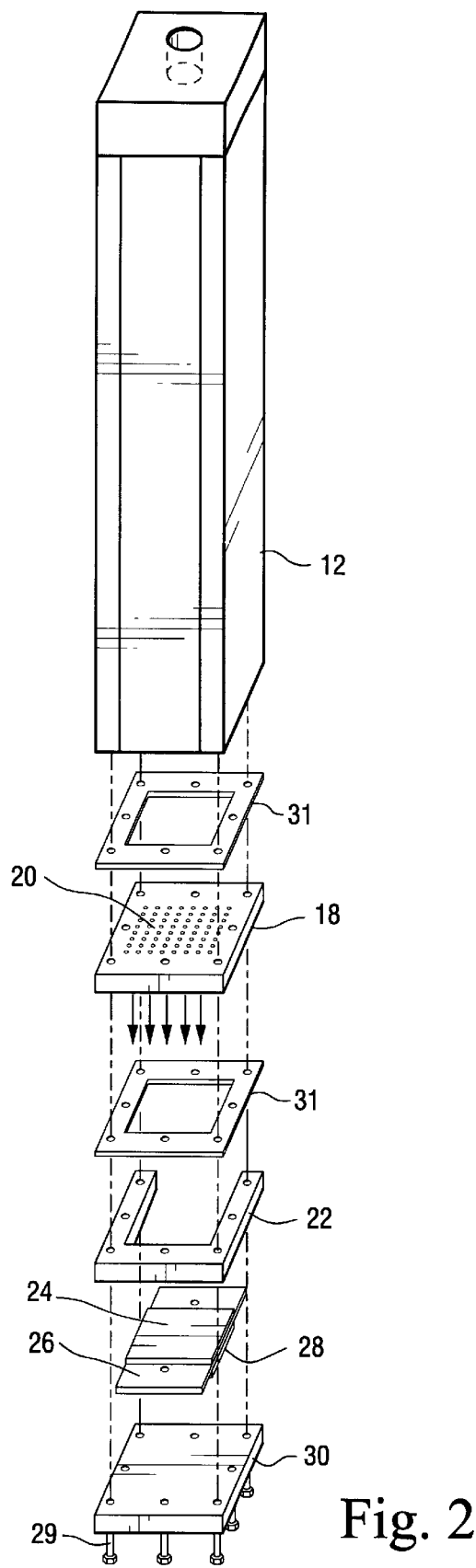
FIG. 2 is an exploded perspective view of the test plenum of FIG. 1.
Figure 3:
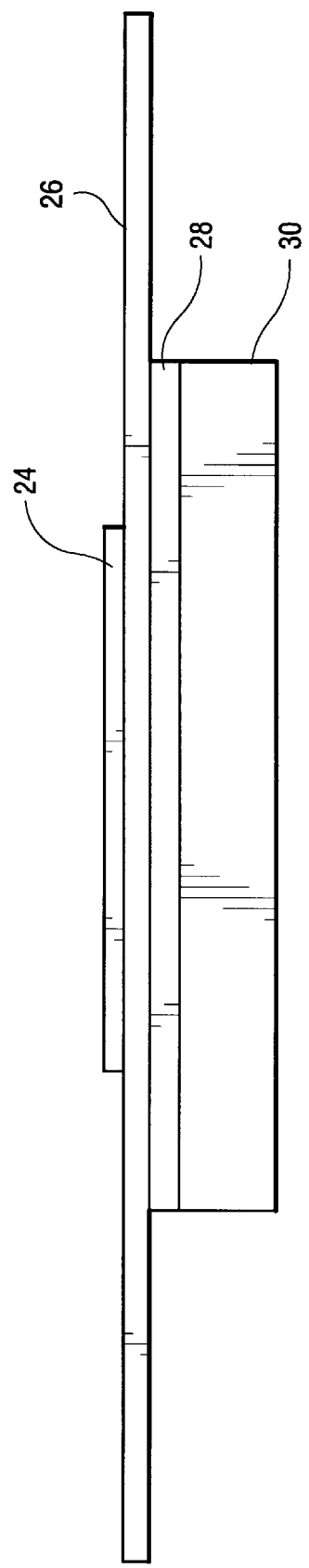
FIG. 3 is an enlarged elevational view of the arrangement of the test plate, heater, liquid crystal and Plexiglas.

Referring to FIG. 2, there is shown an exploded perspective view of the test plenum of FIG. 1. Along the underside of the jet plate 18, a generally U-shaped spacer 22 is provided whereby the air flowing through the orifices 20 of plate 18 flows into the volume defined by the U-shaped spacer. It will be appreciated that the U-shaped spacer 22 is open at one end for exhausting the impingement air as described below. Below the spacer 22, there is provided a test plate 24 extending parallel to the jet plate 18. Orifices 20 may be staggered as show in FIGS. 9 or slotted as show in FIG. 10. A heater plate 26, preferably in the form of a thin Iconel foil heater, is applied along the undersurface of the test plate to provide a constant flux boundary condition. Next, a calibrated liquid crystal sheet 28 is mounted on the side of the heater remote from the test plate. Finally, a cover 30 formed of transparent material, preferably Plexiglas, is placed along the liquid crystal face remote from the heater. The transparent cover 30 acts as insulation to reduce heat losses while enabling visual observation of the temperature fields along the impinging surface. The test plate 24 can be omitted in the case of impingement on a smooth surface where the air impinges directly on the heater surface. Thus, the heater surface, in that instance, also serves as the test plate. A plurality of bolts 29 may be used to secure the spacer 22, test plate 24, heater 26, and Plexiglas 30 to the housing 12. Various gaskets 31 are interposed in this stack-up to seal the chamber 14. The liquid crystal sheet 28 may be secured to the back of the heater 26 using an adhesive material. Although bolts 29 appear to identical in the figure as shown, it should be noted that it is not necessary that they be identical. Also, bolts 29 are made of such material to prevent a short circuit in the apparatus. For example, plastic may be one such material.

Figure 4:
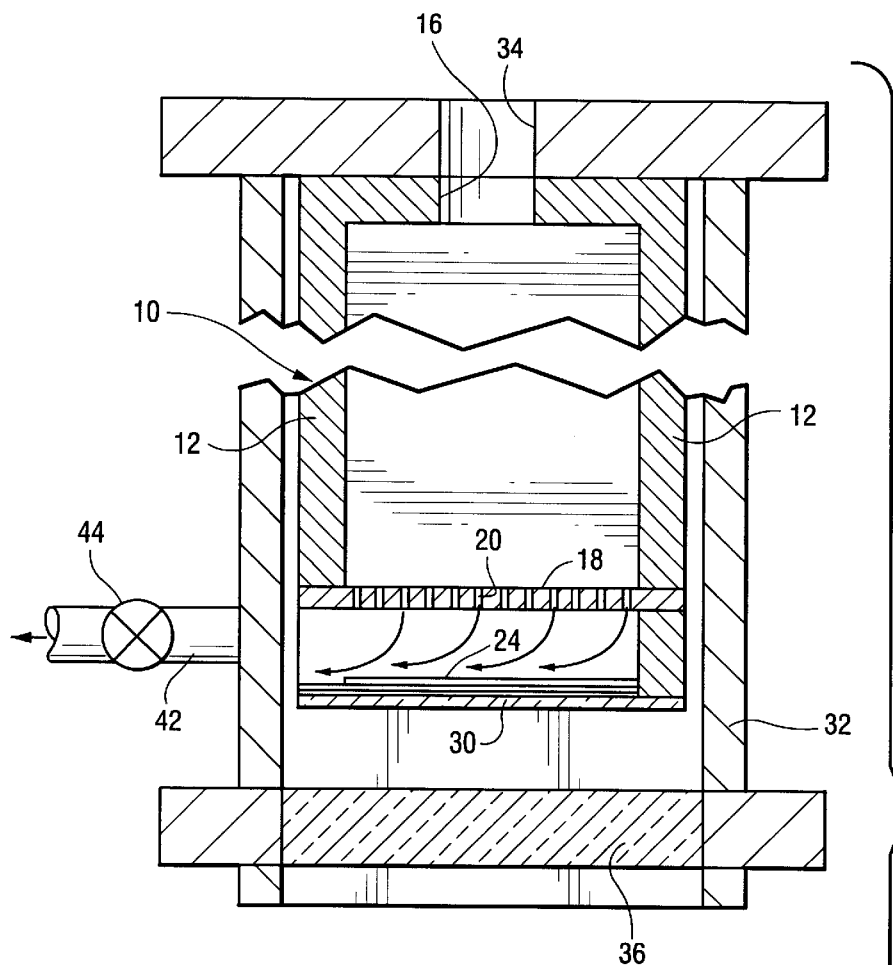
FIG. 4 is a view similar to FIG. 1 illustrating the test plenum within a pressure vessel.
Figure 4:
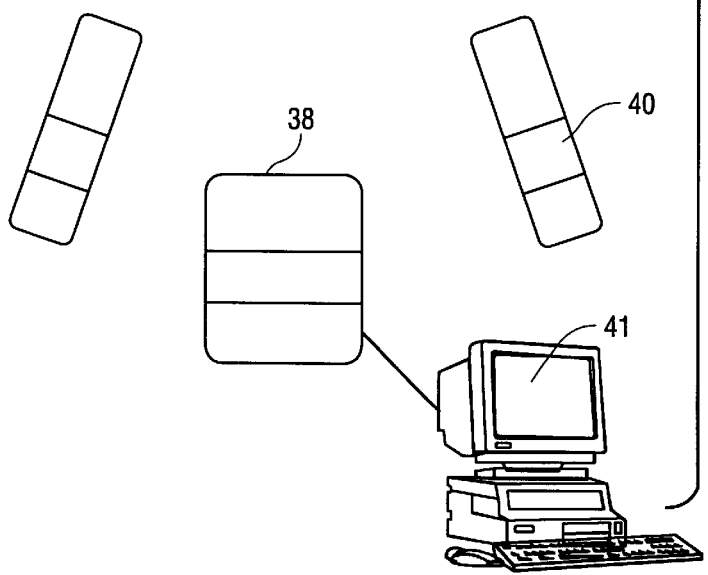

Referring now to FIG. 4, the plenum 10 is disposed within a pressure vessel 32. The inlet 16 of housing 12 lies in communication with an opening 34 at one end of the pressure vessel. The opposite end of the pressure vessel 32 includes a transparent pressure window 36 for viewing the liquid crystal image. A camera 38 is located outside of the pressure vessel 32 for viewing and capturing the images of the liquid crystal sheet/element 28 through a transparent pressure window 36 and the transparent cover 30. Camera 38 may be any image capturing device. Lighting 40 is provided to ensure quality imaging. A computer system 41 having a processor and memory receives images captured by the camera 38 and processes the received images to extract temperature distribution profiles. The computer system 41 further includes software to compute heat transfer coefficients from the temperature distribution profiles, and Nusselt numbers from the heat transfer coefficients. Additionally, the pressure vessel 32 includes an outlet 42 containing a back pressure valve 44. By locating the plenum 10 within a pressure vessel 32, control of the pressure ratio across the test plate 24 is provided. Additionally, the tests may be run at higher jet Reynolds numbers than possible if the air is discharged directly to the atmosphere. The temperature of the air supplied to the pressure vessel 32 is monitored and controlled, by means not shown, to stay within predetermined temperature limits to produce accurate heat transfer coefficient results. For example, a chiller may be used to control the temperature of air entering the plenum.

Figure 9:
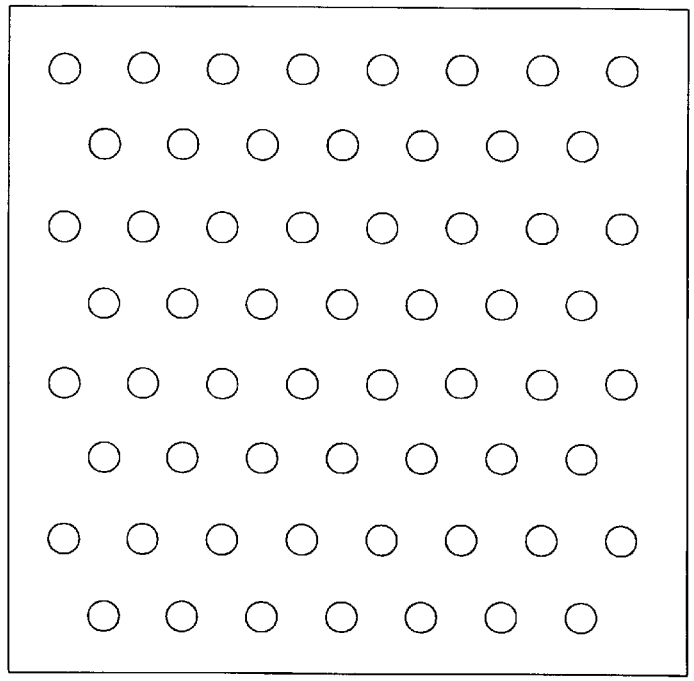
FIGS. 9–10 show various jet plate configurations.
Figure 10:
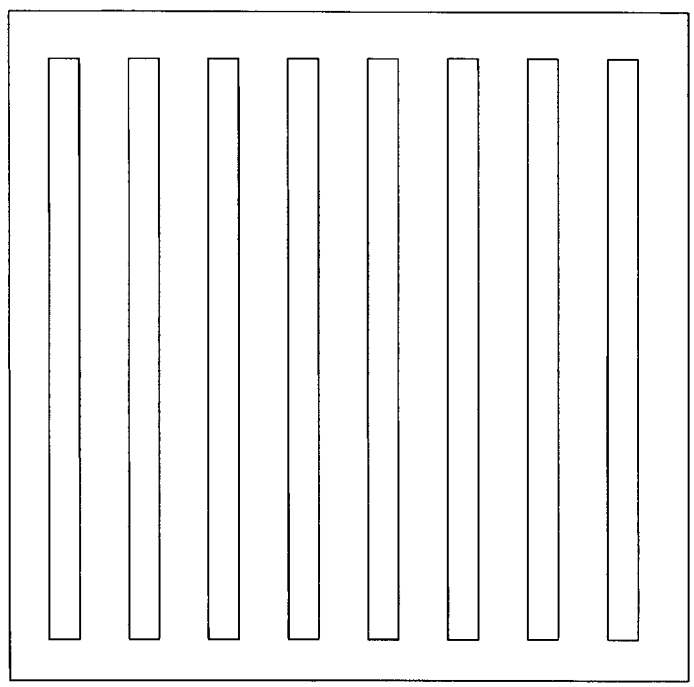

Different jet plates 18 having orifices 20 opening through the plates at different angles may be provided to obtain heat transfer characteristics at various jet impingement angles. Further, the orifices 20 may be provided in any desired array, for example, a square array may be used with constant spacing between the holes in both X and Y directions. The diameter of the orifices 20, of course, may vary, as well as the angle of the orifices relative to the plate, e.g., 30°, 60°, 90°, etc. With the plenum set up as in FIG. 4 within the pressure vessel 32, the air flowing through the orifices 18 impinges on the test plate and is removed via the outlet 42 from the pressure vessel. It will also be appreciated that variable power may be supplied to the heater whereby various heat fluxes in contact with the impingement surface of the test plate 24 may be provided. The surface heat flux is assumed constant under steady state conditions, providing constant heat flux boundary conditions. It is also contemplated to use jet plates having staggered configurations as shown in FIG. 9. Also, slots as in FIG. 10 may be used instead of round circular jets. The present invention is not limited to any specific configurations.

A digital video system is employed to digitally record the liquid crystal temperature profiles in the computer and an image analysis system converts the liquid crystal image data into temperature distributions. The camera 38 may comprise a Sony XC-711 CCD video camera with RGB output. A data translation DT-2871 frame grabber digitizes the RGB video image by converting RGB signals to HSI signals.

Figure 5:
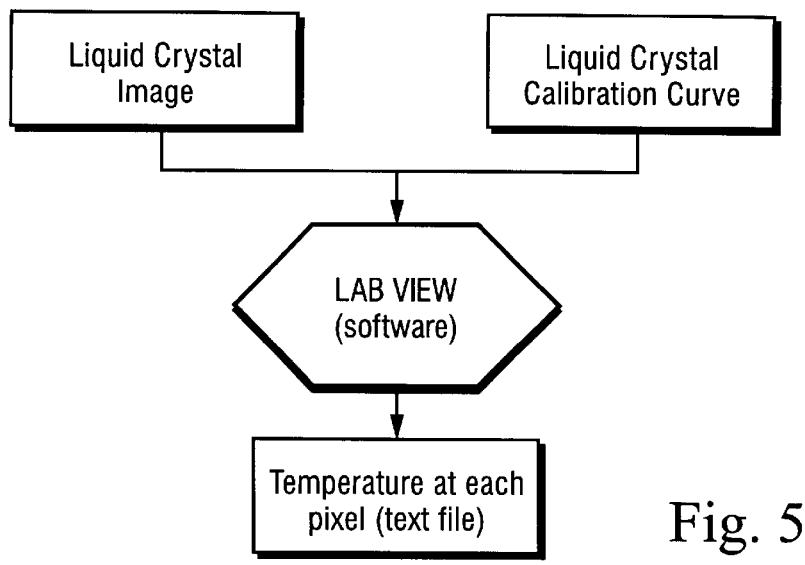
FIG. 5 is a schematic for generating temperature distribution profiles using software loaded into the computer system associated with the test apparatus.

Prior to using the system set forth in FIGS. 1 through 4, the liquid crystal must be calibrated. For example, thermocouples may be embedded at equal distances along the calibration apparatus where liquid crystal strip to be calibrated is located. As the liquid crystal temperature changes along the crystal between hot and cold, the colors of the liquid crystal progress in the order of clear-red-yellow-green-blue-violet-clear. The colors of the liquid crystal are then correlated to the temperatures measured by the embedded thermocouples and a calibration data/curve is determined. This calibration data is loaded into a test apparatus computer system 41 (FIG. 4) as shown in FIG. 5 when the test apparatus is employed to measure temperatures using this same particular liquid crystal. It should be noted that the calibration process must be performed if any other liquid crystal sheet/material is incorporated into the test apparatus.

To measure the local heat transfer distribution on the surface, an image of the liquid crystal coloration is captured and digitized. As generally illustrated in the schematic of FIG. 5, the image data is corrected using the calibration data stored in the computer system 41 (FIG. 4). From the corrected data, a text file is created containing temperature at each pixel in the captured image, the text file constituting a two-dimensional array of data with the point of intersection of each row and column representing a single pixel. Using another software package stored in computer system 41 (FIG. 4), the temperature data is converted into heat transfer coefficients and Nusselt numbers.

In dealing with numerical simulations of large and complex systems involving energy transport in both fluids and solids, the heat transfer at the interfaces is of great importance. The Nusselt number couples the energy transport between a solid and a fluid, and serves as a tool in engineering and design of large systems where heat-transfer considerations are of considerable interest. The Nusselt number, as a function of the Reynolds number, may be needed for accurate numerical modeling of a system response. In order to extract the Nusselt number as a function of the Reynolds number, a series of measurements and optimizations for varying response conditions are performed. The optimized Nusselt numbers form the basis for either a look-up table or an empirical tailor made expression for the Nusselt number as a function of the Reynolds number.

For forced convection of a single-phase fluid with moderate temperature differences, the heat flux per unit area is nearly proportional to the temperature difference. Thus, Newton's law of cooling is represented by the equation $$q \alpha \Delta T \tag{1}$$

Equation (1) may be written as $q = h \Delta T$, where h is the heat transfer coefficient. A dimensionless form of "h" is the Nusselt number Nu, defined as the ratio of convection heat transfer to fluid conduction heat transfer under similar conditions.

In order to determine the heat transfer distribution on the entire impingement surfaces, several images are taken at various heat flux levels to obtain a color change in each element of the liquid crystal. These images are essentially superimposed and averaged to yield the heat transfer distribution on the entire surface. This assumes that the heat transfer coefficients are not a function of heat flux. With that assumption, it is possible to obtain an overall heat transfer coefficient distribution by averaging the partial distributions of the individual images. That is, the heat transfer coefficient distribution is determined at each heat flux level and recorded. The average heat transfer coefficient is then obtained by averaging the heat transfer coefficient of each pixel or each array element over all images taken. Once the overall transfer coefficient is obtained, the overall Nusselt number distribution for the surface based on this average heat transfer coefficient, average thermal conductivity of air and the jet diameter is obtained. The foregoing steps may be repeated for each jet plate configuration at each Reynolds number as desired.

Figure 6:
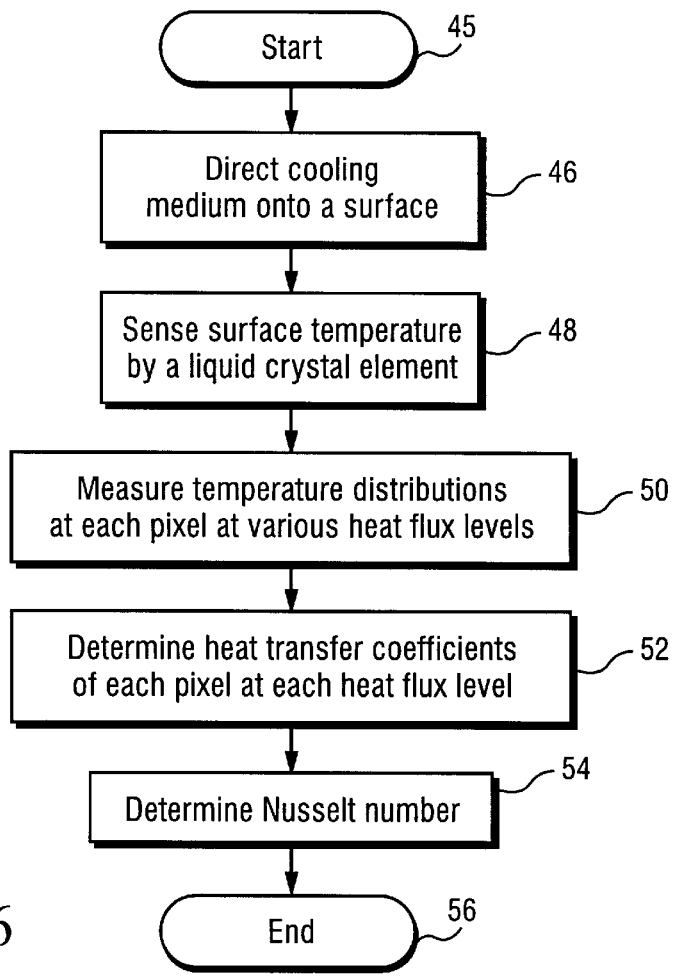
FIG. 6 is a high level schematic illustrating the process steps for determining the heat transfer coefficients and the Nusselt number in accordance with a preferred embodiment of the present invention.

FIG. 6 shows a high level schematic illustrating the process steps for determining the heat transfer coefficients and the Nusselt number in accordance with a preferred embodiment of the present invention. Here, a cooling medium is jet directed to impinge on an object surface in order to cool the same as generally indicated at step 46. The surface temperature of the object is sensed using a liquid crystal element at step 48. After sensing the surface temperature, temperature distributions at each pixel location are measured for various heat flux levels, thus creating a temperature distribution profile as indicated at step 50. From the temperature distribution profiles, heat transfer coefficients of each pixel at each heat flux level are determined at step 52. A Nusselt number is determined for each heat transfer coefficient at step 54.

Figure 7:
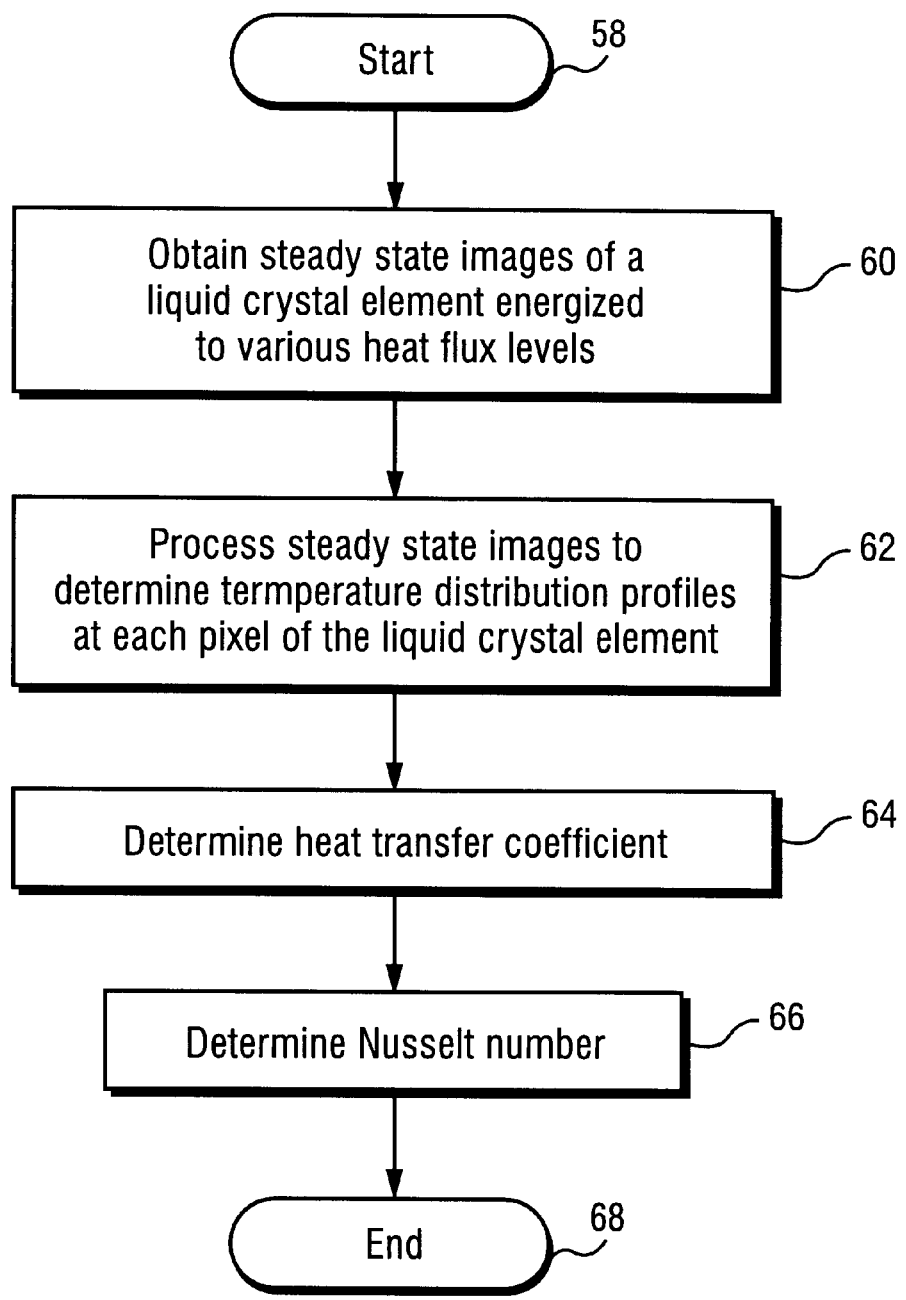
FIG. 7 is another flow schematic to determine the Nusselt number in accordance with a preferred embodiment of the present invention.

FIG. 7 shows another flow schematic to determine the Nusselt number in accordance with a preferred embodiment of the present invention. Here, steady state images of a liquid crystal element are obtained at various heat flux levels as shown in step 60. The obtained steady state images are processed to determine temperature distribution profiles at each pixel location of the liquid crystal element as indicated at step 62. From the temperature distribution profiles, heat transfer coefficients are determined at step 64, and subsequently, Nusselt numbers are determined from the heat transfer coefficients as indicated at step 66.

Figure 8:
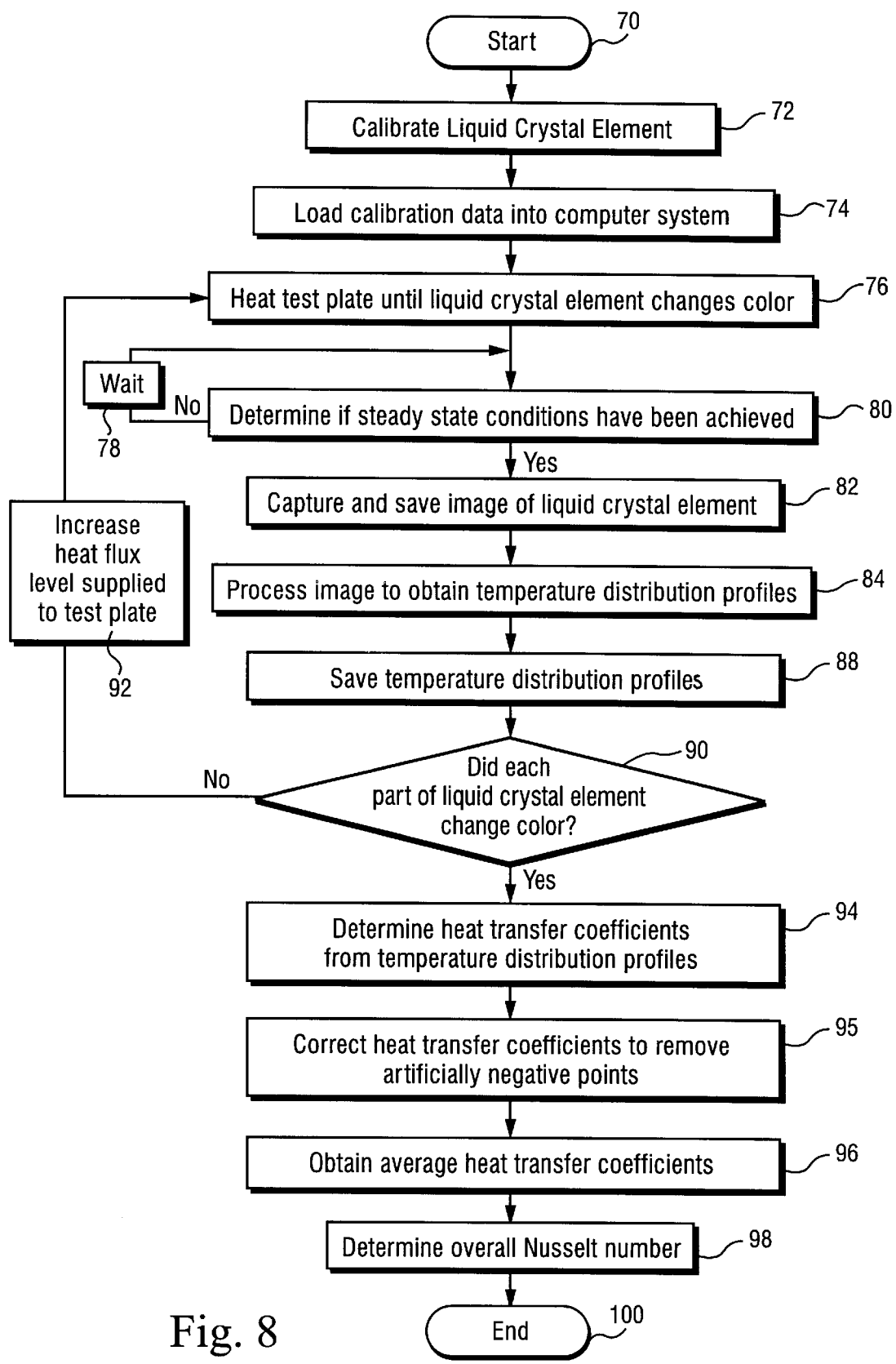
FIG. 8 is a detailed flow schematic to determine an overall Nusselt number from the heat transfer coefficients in accordance with a preferred embodiment of the present invention.

FIG. 8 is a detailed flow schematic to determine an overall Nusselt number from the heat transfer coefficients in accordance with a preferred embodiment of the present invention. In this schematic, a liquid crystal element, used for sensing temperature distribution of an object surface, is calibrated at step 72. The calibrated data is loaded into a computer system 41 (FIG. 4) associated with the test apparatus as indicated at step 74. The liquid crystal element is heated to a first heat flux level until a portion of the liquid crystal element changes color as indicated at step 76. During step 80, a determination is made to see if a steady state condition has been achieved by the liquid crystal element. In the event a steady state condition is not achieved, the liquid crystal element is not energized to a higher heat flux level. Rather, the test apparatus is held in a waiting state as shown at step 78 until a steady state condition is achieved. Once a steady state condition is achieved, an image of the liquid crystal element is captured and saved as shown at step 82, and the image is processed to obtain temperature distribution profiles as at step 84. The process steps of applying progressively increasing heat flux levels to the liquid crystal element is repeated until each part of the liquid crystal element changes color as show at step 90, and the temperature distribution profiles and heat transfer coefficients are determined for each heat flux level as described above. The heat transfer coefficients are corrected to remote any artificial negative points as indicated at step 95. The corrected heat transfer coefficients are averaged at step 96, and an overall Nusselt number is determined from the averaged heat transfer coefficient at step 98. The process steps indicated by FIG. 8 may be repeated for each jet plate configuration at each Reynolds number as desired.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of measuring local heat transfer characteristics of an object surface, the method comprising the steps of:
    (a) flowing a cooling medium onto the surface;
    (b) sensing the temperature of the surface by juxtaposing a broadband width liquid crystal sheet and the surface;
    (c) measuring temperature distributions of each pixel of the liquid crystal sheet at various heat flux levels;
    (d) processing the temperature distributions to obtain temperature distribution profiles at each heat flux level;
    (e) determining heat transfer coefficients of each pixel at each heat flux level
    (f) determining an average heat transfer coefficient profile at each pixel; and
    (g) performing steps (a), (b) and (c) at steady state conditions.

2. A method according to claim 1 including determining an overall Nusselt number from the average heat transfer coefficient profile.

3. A method according to claim 1, further comprising:
    calibrating the liquid crystal element prior to the processing step (d) and independently of the object surface.

4. A method according to claim 1, further comprising:
    saving the temperature distribution profiles, and filtering the heat transfer coefficients at each pixel to remove artificially negative data points.

5. A method according to claim 1 wherein step (b) includes juxtaposing a liquid crystal sheet having a broadband of temperature of about 5°.

6. In an apparatus comprising a heater element and a liquid crystal sheet juxtaposed in temperature sensing relation to an object surface, a method of measuring local heat transfer distribution along the surface comprising the steps of:
    (a) directing a cooling gas through a plurality of openings forming plural jets of cooling air impinging on the object surface;
    (b) obtaining steady state images of said liquid crystal sheet as a function of the sensed temperature of the cooled object surface at various heat flux levels;
    (c) processing said steady state images to determine temperature distribution profiles at each pixel along said liquid crystal sheet;
    (d) determining heat transfer coefficients for each temperature distribution profile; and
    (e) determining an average heat transfer coefficient profile.

7. A method according to claim 6 including calculating an overall Nusselt number from the average heat transfer coefficient profile.

8. A method according to claim 6 including saving said temperature distribution profiles and filtering the temperature distribution profiles at each pixel to remove negative data points.

9. A method according to claim 6 including juxtaposing the liquid crystal sheet and the object surface wherein the liquid crystal sheet has a broadband of temperature of about 5°.

10. A method for measuring local heat transfer distribution of an object surface, the method comprising the steps of:
   (a) directing cooling air through a plurality of openings forming plural jets of cooling air impinging on the object surface;
   (b) providing a liquid crystal sheet on a side of a heater element remote from the object surface;
   (c) energizing said heater element to various heat flux levels;
   (d) measuring temperature distributions of various pixels of said liquid crystal sheet at the various heat flux levels;
   (e) processing said temperature distributions to obtain temperature distribution profiles; and
   (f) obtaining heat transfer coefficients for each distribution profile.

11. A method according to claim 10 including determining a Nusselt number for each heat transfer coefficient.

12. A method according to claim 10 wherein step (d) is performed at steady state conditions and the liquid crystal sheet provided in step (b) has a broad temperature band of 5° or less, and including averaging said heat transfer coefficients to obtain an average heat transfer coefficient and calculating an overall Nusselt number from said average heat transfer coefficient.

13. A method according to claim 10, comprising:
   calibrating the liquid crystal sheet prior to the energizing step.

14. A method according to claim 10 including providing a sheet of transparent plastic material along a side of said liquid crystal sheet remote from said heater element.

15. An apparatus for measuring local heat transfer distribution of an object surface, comprising:
   a heater element for providing heat flux;
   a test plate disposed on a surface of the heater element for receiving impinging cooling air;
   a liquid crystal sheet on a side of said heater element remote from said surface;
   an insulating material in contact with said liquid crystal sheet and remote from said heater element; and
   means for determining heat transfer coefficients distribution from said liquid crystal sheet.

16. The apparatus as in claim 15, wherein said heater element is a thin foil heater.

17. The apparatus as in claim 15, wherein said insulating element is formed of a transparent material.

18. The apparatus of claim 15, further comprises:
   a liquid crystal video thermographic system for capturing images of the liquid crystal sheet at various heat flux levels.

19. The apparatus of claim 18, further comprises:
   a computer system for controlling and monitoring various elements of the apparatus.

20. The apparatus of claim 19, wherein said computer system comprises a memory device to store images of the liquid crystal sheet.

21. An apparatus for measuring local heat transfer distribution of an object surface, comprising:
   a liquid crystal sheet;
   a heater element for heating the liquid crystal sheet to various heat flux levels;
   said liquid crystal sheet disposed adjacent to the heater element for measuring heat transfer distributions of the object surface;
   means for capturing images of said liquid crystal sheet at each heat flux level; and
   means for determining heat transfer coefficients from the captured images.

22. An apparatus for measuring local heat transfer characteristics of an object surface, comprising:
   means for flowing a cooling medium onto the surface;
   means for heating and sensing the temperature of the heated surface by juxtaposing a broadband liquid crystal sheet and the surface;
   means for measuring temperature distributions of each pixel of the liquid crystal element at various heat flux levels and at steady state conditions;
   means for processing the temperature distributions to obtain temperature distribution profiles at each heat flux level;
   means for determining heat transfer coefficients of each pixel at each heat flux level; and
   means for determining an average heat transfer coefficient profile at each pixel.

23. The apparatus of claim 22, further comprises:
   means for determining Nusselt numbers from the average heat transfer coefficient profiles.

* * * * *